United States Patent [19]

Lilja et al.

[11] Patent Number: 4,848,376
[45] Date of Patent: Jul. 18, 1989

[54] TOBACCO COMPOSITIONS, METHOD AND DEVICE FOR RELEASING ESSENTIALLY PURE NICOTINE

[75] Inventors: Jan E. Lilja, Kristianstad; Sven E. Nilsson, Helsingborg, both of Sweden

[73] Assignee: AB Leo, Helsingborg, Sweden

[21] Appl. No.: 148,553

[22] Filed: Jan. 26, 1988

Related U.S. Application Data

[62] Division of Ser. No. 882,929, Jun. 19, 1986, Pat. No. 4,776,353.

[30] Foreign Application Priority Data

Nov. 1, 1984 [SE] Sweden .................................. 8405479

[51] Int. Cl.⁴ ............................................. A24B 15/28
[52] U.S. Cl. ....................................... 131/352; 131/329; 131/335
[58] Field of Search ............... 131/352, 329, 359, 369, 131/353, 335

[56] References Cited

U.S. PATENT DOCUMENTS

| | | | |
|---|---|---|---|
| 896,124 | 8/1908 | Lindenberger et al. | 131/297 |
| 999,674 | 8/1911 | Sartig | 131/297 |
| 2,104,266 | 1/1938 | McCormick | 131/329 |
| 2,972,557 | 2/1961 | Toulmin Jr. | |
| 3,292,636 | 12/1966 | Mays | |
| 4,141,369 | 2/1979 | Burruss | 131/330 |
| 4,219,032 | 8/1980 | Tabatznik et al. | |
| 4,284,089 | 8/1981 | Ray | |
| 4,303,083 | 12/1981 | Burruss Jr. | |
| 4,340,072 | 7/1982 | Bolt | 131/ |

FOREIGN PATENT DOCUMENTS

| | | |
|---|---|---|
| 0155514 | 2/1985 | European Pat. Off. |
| 116941 | 1/1900 | Fed. Rep. of Germany |
| 2099824 | 3/1972 | France |
| 1116644 | 6/1968 | United Kingdom |
| 1316987 | 5/1973 | United Kingdom |

*Primary Examiner*—V. Millin
*Attorney, Agent, or Firm*—Gordon W. Hueschen

[57] ABSTRACT

Novel tobacco compositions which—when subjected to an elevated temperature below the combustion temperature the tobacco—liberates essentially pure nicotine.

16 Claims, 2 Drawing Sheets

U.S. Patent   Jul. 18, 1989   Sheet 1 of 2   4,848,376
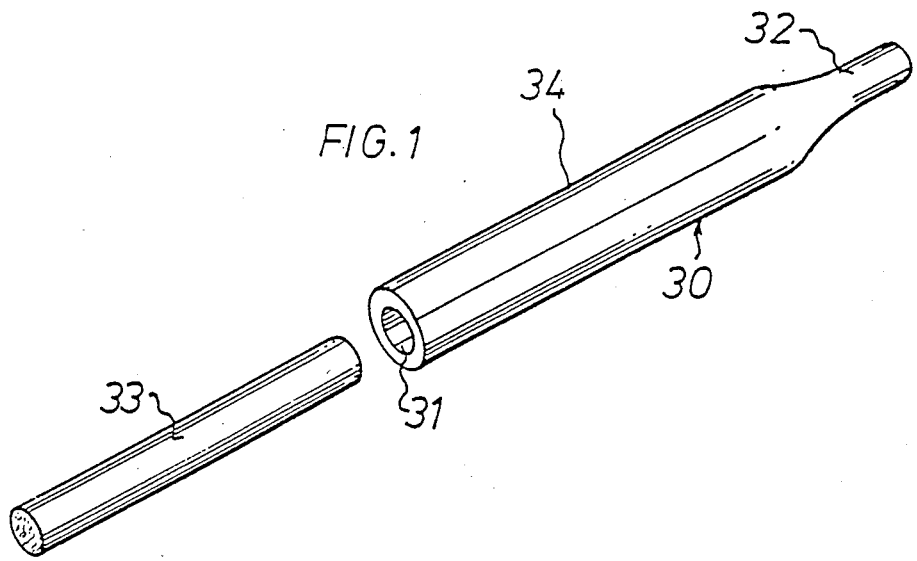
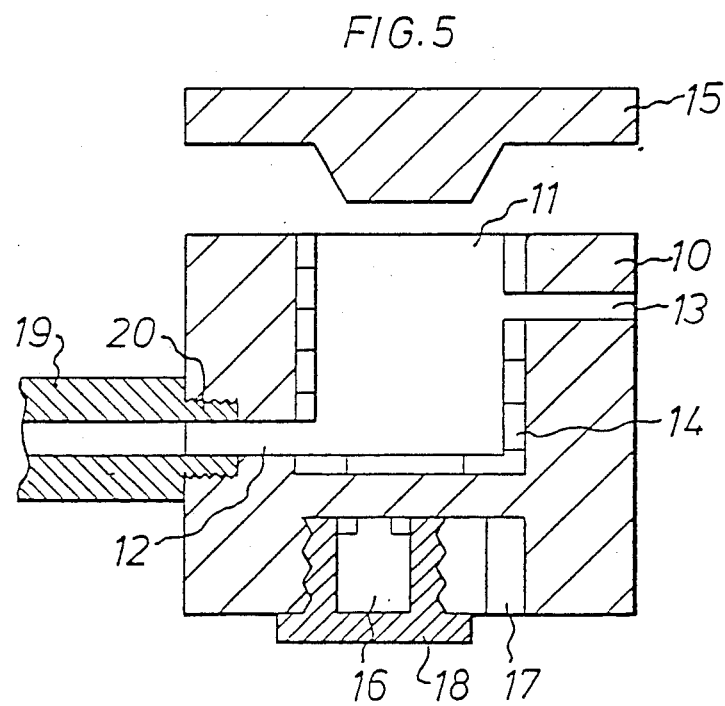

TOBACCO COMPOSITIONS, METHOD AND DEVICE FOR RELEASING ESSENTIALLY PURE NICOTINE

This is a division of application Ser. No. 882,929, filed June 19, 1986 now U.S. Pat. No. 4,776,353.

The present invention concerns tobacco compositions and a non-combustion method of liberating essentially pure nicotine from such compositions. It also includes a device for carrying out the method.

It is now widely recognized that smoking can be a major health hazard. This hazard can be cut down by reducing or eliminating smoking, but smokers find this extremely difficult and it is generally accepted that this difficulty is caused by nicotine-dependence. While the presence of nicotine in tobacco smoke is considered a risk factor, there are other, more important risk factors in the substances formed during the combustion of tobacco such as carbon monooxide, tar products, aldehydes and hydrocyanic acid.

One way of eliminating risk factors other than nicotine is disclosed in the U.S. Pat. No. 4,284,089. According to this patent pure nicotine vapors are obtained when air is drawn through a device containing a nicotine mixture disposed within an absorbent member. The nicotine mixture may be selected from the group consisting of nicotine (d), nicotine (1), nicotine (d,1), nicotine salts and nicotine esters.

The U.S. Pat. Nos. 4,141,369 and 4,219,032 disclose devices for non-combustion utilization of tobacco. These devices are concerned with designs of the devices different from that according to the present invention. Besides, no information is given on the amount or the purity of nicotine obtained when gas from these devices is inhaled.

OBJECTS OF THE INVENTION

It is an object of the invention to provide a novel tobacco composition which—when air is drawn therethrough for inhalation purposes—liberates essentially pure nicotine.

A second object of the invention is to provide a non-combustion method of liberating essentially pure nicotine for inhalation purposes from the novel tobacco composition.

A third object of the invention is to provide a non-combustion method of liberating essentially pure nicotine from the novel tobacco compositions according to which essentially the same rate and amount of nicotine release is obtained at inhalation as when smoking the corresponding amount of tobacco.

A fourth object is to provide a non-combustion method of liberating essentially pure nicotine from the novel tobacco compositions, which method requires only moderately elevated temperatures at which essentially no thermal decomposition products are formed.

A fifth object of the invention is to provide a device that can be used for the inhalation of nicotine from the novel tobacco composition.

A sixth object of the invention is to provide a nicotine releasing product that can be handled in substantially the same way as the tobacco products presently used, which is not clumsy or complicated and which comprises the device having the novel tobacco compositions included therein.

SUMMARY OF THE INVENTION

The invention concerns novel tobacco compositions liberating essentially pure nicotine when air is drawn through the composition for e.g. inhalation purposes. The compositions include as major constituents tobacco, water and a basic substance. Optionally oils, detergents and/or flavoring agents may be added to the compositions.

The invention also concerns a non-combustion method of liberating essentially pure nicotine from these tobacco compositions, comprising the steps of mixing a tobacco material optionally containing oils, detergents and/or flavoring agents with water and a basic substance optionally dissolved or dispersed in the water. The composition obtained is heated to a temperature below the combustion temperature of the tobacco but sufficiently high to liberate nicotine in an amount and at a rate similar to that obtained at smoking when air is drawn through the composition.

The device for the release and administration of nicotine according to the invention comprises receiving means (10, 30) which has a space (11, 31) provided with an inlet and an outlet (12, 36) and in which a matrix such as the novel tobacco compositions containing the nicotine is insertable, and a mouthpiece (19, 32) communicating with the outlet (12, 36) of said receiving space. The device is characterized by a heating element (14; 40; 46, 47; 49, 50) associated with said receiving space (11, 31), said element being adapted upon manual activation to produce heat in said space (11, 31), and means (17; 41) for restricting the temperature in the receiving space (11, 31) to a predetermined value below the combustion temperature of the matrix.

DETAILED DESCRIPTION OF THE INVENTION

The tobacco compositions according to the invention includes a mixture consisting essentially of tobacco, water and a basic substance. The water might be added to the tobacco in the form of ordinary drinking water. Before mixing the tobacco and water it might be preferable to dissolve or disperse the basic substance in the water. The tobacco compositions according to the invention might also contain the water in the form of water-containing salt or in the form of heatsensitive microcapsuls. Examples of watercontaining salts are soda or zeolites. Other representative examples are calcium hydrates such as calcium monohydrate, dihydrate or hexahydrate, sodium pyrophosphates such as $Na_4P_2O_7 10 H_2O$ or $Na_4P_2O_7 6 H_2O$, or sodium orthophosphates such as $Na_2HPO_4 7 H_2O$ or $Na_2HPO_4 12 H_2O$. The "dry" water contained in the watercontaining salts and in the microcapsuls is set free at the elevated temperature required according to the invention and a wet basic tobacco composition is obtained. This composition is capable of releasing nicotine at inhalation in an amount and at a rate similar to that which is obtained when smoking.

Special advantages can be obtained by using $Na_2CO_3 10 H_2O$. This salt contains water to such an amount that it will not be necessary to add free water at the same time as a basic substance necessary to get the required pH is provided. In order to obtain an effective amount of nicotine, i.e. an amount of the same magnitude as when smoking, it is required that the pH of the tobacco compositions according to the present invention exceeds 7. Preferably the pH shall exceed 8 and most preferably 8.8. There seems to be no need to use a pH above 12 and with ordinary tobacco there seems to be no need to use compositions having a pH above 10. However, the upper limit of the pH can be decided separately and according to taste, desired nicotine release and other parameters known to the man skilled in the art.

As pointed out previously a certain amount of water is necessary in order to get a satisfactory nicotine release. It should be pointed out in this context that tobacco contains water in amounts varying between 5 and 25 percent (weight/weight) of the tobacco. For the same reasons as discussed above as regards the pH it is obvious that the water content of the tobacco composition according to the invention can vary within a wide range. Good results as regards the nicotine release have been obtained with tobacco compositions having a water content varying between 0.25 and 7, preferably between 1 and 5, g water per g ordinary tobacco. At present the most favourable results have been obtained with about 3 g water/g ordinary tobacco.

In addition to soda the basic material might be selected from a wide variety of substances which, of course, shall be non-toxic and preferably tasteless or palatable. Examples of suitable basic substances to be incorporated in the tobacco compositions according to the invention are carbonates or hydroxides of sodium, potassium or calcium.

Various additives can be incorporated into the tobacco compositions according to the invention in order to improve its characteristics. Examples of such additives are oils, e.g. silicone oils and paraffine oils, detergents, e.g. polyoxyethylene ethers such as Brij TM or Tween TM and flavoring agents, e.g. menthol, anis.

The present invention also concerns a method for liberating essentially pure nicotine from tobacco for inhalation purposes. This method comprises the steps of mixing a tobacco material optionally containing oil, detergent and/or flavoring agents with water and a basic substance optionally dissolved or dispersed in the water and heating the composition obtained to a temperature sufficient to liberate an efficient amount of nicotine but below the combustion temperature of the tobacco. As previously described the water may be in the form of a water containing salt or in the form of heatsensitive microcapsules and optionally the water and the basic substance may be provided in the same substance, e.g. soda.

As described above the efficient amount of nicotine is an amount corresponding to the amount that the smoker obtains when smoking. The temperature required in order to obtain this amount on the composition used can be easily determined by simple experiments. Usually the temperature required varies between 30° and 200° C. and preferably between 50° and 100° C. The most favourable results have been obtained by using temperatures between 70° and 80° C. In order to reach the desired temperature rapidly it might be suitable to subject the tobacco compositions to a higher temperature initially. When the water is present in bound form in the tobacco composition free water will be liberated upon heating.

The following tests illustrate the release of nicotine from the compositions according to the invention:

Small glass columns were packed with tobacco compositions according to the invention. The tobacco compositions consisted of 1 g of tobacco that had been soaked with 2 ml of a saturated aqueous sodium carbonate solution. Untreated tobacco was used as reference. Air (1 liter) was blown through each column at a rate of 50 ml/3-4 Ts with a syringe and the released nicotine was collected in sulphuric acid solution. UV absorption measurements indicated that essentially pure nicotine was liberated.

The following results were obtained:

| Tobacco composition | Temperature °C. | Released nicotine mg/l air |
| --- | --- | --- |
| According to the invention | 35 | 0.05–0.10 |
| According to the invention | 55 | approx. 0.50 |
| According to the invention | 75 | approx. 2.20 |
| Untreated | 75 | approx. 0.03 |

The bioavailability of nicotine, i.e. the blood plasma nicotine levels, after inhalation of air from the glass columns prepared as described above at 65° C. and 75° C., respectively was also investigated. The test persons had abstained from smoking or having nicotine in any other way for 12 h before the test.

The following plasma peak values were obtained:

| Temperature ° C. | Plasma nicotine ng/ml |
| --- | --- |
| 65 | 5 |
| 75 | 10–15 |

A device for the release and administration of nicotine from the composition described above should comply with two important requirements. First, it must be able to produce heat of a temperature which is below the combustion temperature of the matrix, i.e. tobacco composition, and, secondly, it must be small and easy to transport and handle. Preferably, it should have the approximate size and shape of a cigarette holder or a pipe, i.e. have the appearance of an object to which the smoker is accustomed.

In the enclosed drawings, there are shown examples of suitable devices.

FIG. 1 is a perspective view of a device designed as a "cigarette" holder, together with a "cigarette", by which is meant a composition of the present invention as herein defined, in the form of a more or less conventional cigarette, with or without an external wrapper of paper, plastic or the like.

FIG. 5 is a sectional view of a device resembling a pipebowl.

In FIG. 1, the device according to the invention is in the form of cigarette holder 30 defining a cylindrical space 31 which is open at one end of the holder 30 and so dimensioned that an untipped cigarette 33 is insertable therein substantially in its entirety with suitable friction. At the opposite end, the holder 30 is designed with a mouthpiece 32. It appears that the cigarette holderlike device does not differ to any major extent from a conventional cigarette holder.

Figure 2:
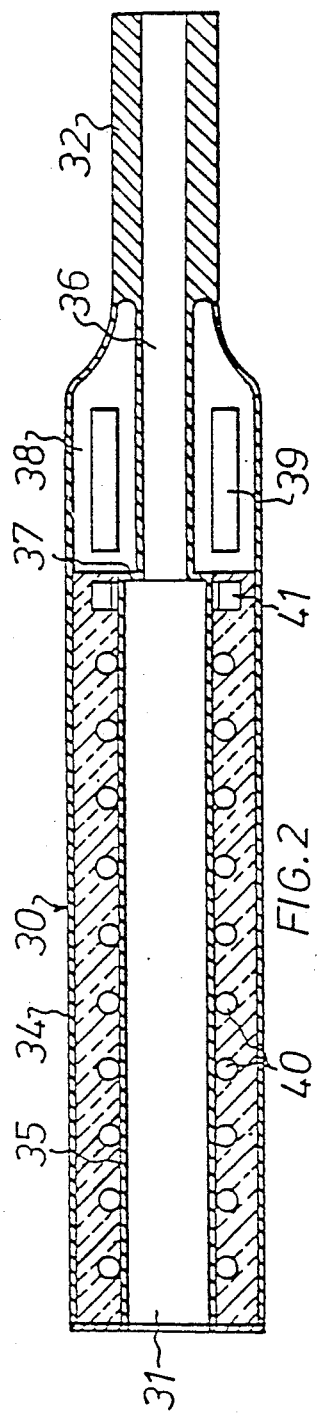
FIGS. 2, 3 and 4 are sectional views of different designs of the device according to FIG. 1.

The device 30 may take the form of many different embodiments to fulfil the objects of the invention. According to FIG. 2, the peripheral wall of the opening 31 and an outer wall 34 define between them a space of annular cross-section having a length corresponding to that of the "cigarette" 33. At its end remote from the insertion end, the opening 31 merges into an opening 36 of reduced cross-section via an abutment 37 restricting the depth of insertion of the "cigarette" 33. The annular channel defined between the walls 34, 35 is slightly widened in the area between the abutment 37 and the mouthpiece 32 to provide room in this widened space 38 for an electric battery 39. This battery 39 is connected over a switch (not shown) to a heating coil 40 surrounding the wall 35 defining the opening 31. In the lines (not shown) between the battery 39 and the coil 40, there is connected a circuit comprising a temperature sensor 41, preferably also comprising predetermined temperature maximizing and minimizing means (not shown). In the use of the holder according to FIG. 2, a "cigarette" 33 is introduced in the opening 31 and the switch (not shown) is activated so that current is supplied to the coil 40 which then supplies heat to the "cigarette" 33 in the space 31. When the predetermined maximum temperature has been reached, this is detected by the sensor 41 which disconnects the battery 39 and reconnects it again when the lower temperature minimum is reached. The temperature in the space 31 can be maintained by means of the illustrated device within a desired narrow temperature range. The Figure merely illustrates the main parts of the device schematically whereas such components as switches, leads, etc., are not illustrated inasmuch as the device can be modified in many different ways within the scope of the invention and the details may vary from one embodiment to another and because such means as are not illustrated are conventional in the art.

Figure 3:
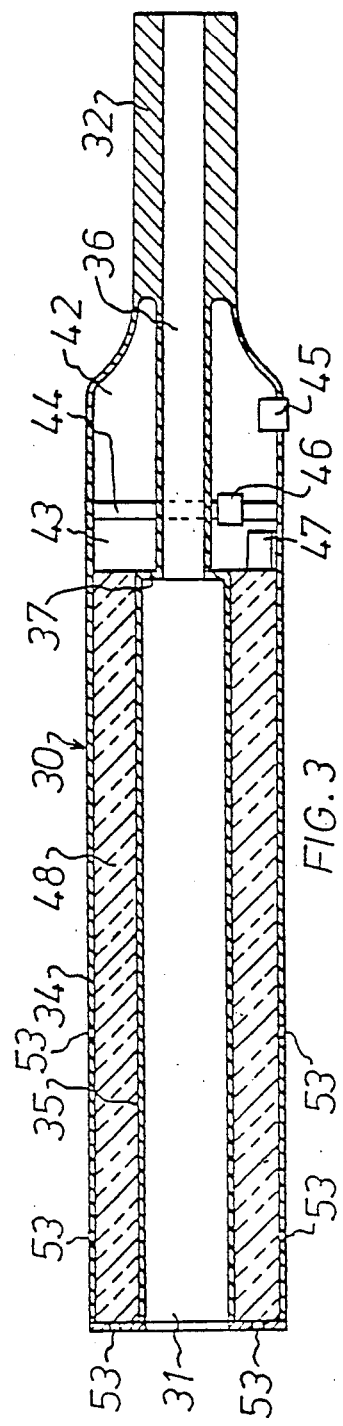

FIG. 3 illustrates another embodiment of the invention, in which the electric heating device has been replaced by a gas burner device. Thus, the walls 34 and 35 define between them a chamber 42 which can be filled with gas through a conventional charging valve 45, e.g., of the type used in cigarette-lighters. Between the walls, there is arranged a further chamber 43 accomodating an igniting device 47 which may also be of the same type as employed conventionally in cigarette-lighters. The two chambers are separated by a partition 44 in which a flow control valve 46 for controlling the flow of gas into the chamber 43 (and then into material 48) is disposed. The remainder of the space between the walls 34 and 35 up to the cigarette insertion end is filled with a suitable, incombustible material which is gas-permeable. To this end, use may be made of different ceramic materials in a suitable design or quite simply suitably packed temperature-stable, high surface area materials such as glass fibres, particles, or shreds, terracotta, mineral wool or the like. The space between the walls 34, 35 is sealed at the cigarette insertion end but has vent openings 53 to allow air and oxygen intake and gas combustion and exhaust. In the use of this embodiment of the device the "cigarette" 33, as in the preceding case, is inserted in the space 31 and gas is thereafter supplied to the chamber 42 through the valve 45, if so required. The gas flows into the chamber 43 with the igniting means 47 through the valve 46 and is there ignited by manually activating the igniting means 47. The hot gases then flow through the gas-permeable material 48 along the space 31 and enter the ambient atmosphere through the openings 53. The temperature in the space 31 is adjusted by means of the valve 46 which allows the passage of a predetermined amount of gas per unit of time, and optionally by solution of the material 48 and the gas permeability factor thereof. When the gas permeable material 48 is ceramic it is possible to preselect the number and size of the interstices thereof per unit area and thereby to determine the rate of gas flow therein and therethrough and the rate of gas permeation thereof, and thus also the maximum attainable temperature, so that a separate temperature control can be eliminated and a desired minimum temperature maintained by rate and amount of suction applied so long a gas is available in chamber 42. With other gas-permeable materials, the temperature control is not inherently "built-in" and separate temperature control means should accordingly be provided. When the gas-permeable material employed is non-catalytic or catalytic and wholly or partially self-igniting, then no igniting means is necessary whereas, when no part of the gas-permeable material 48 is self-igniting, then an ignition means 47 is required.

Figure 4:
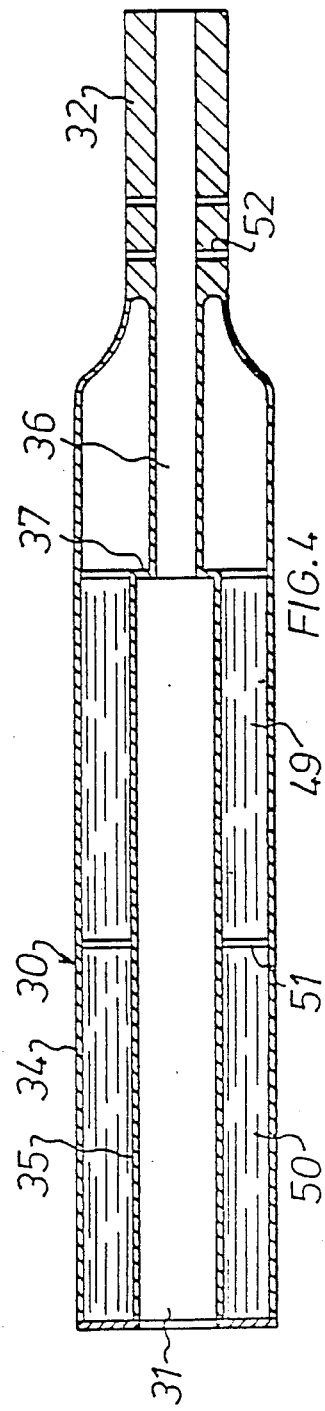

FIG. 4 illustrates a very simple embodiment of the device according to the invention in which the required heat is produced by means of two liquids 49 and 50 which are enclosed in the space between the walls 34 and 35 and separated by means of a partition 51. The liquids 49, 50 are selected from the group of liquids which produce heat when mixed with each other. In the device according to FIG. 4, the part of the device containing the opening 31 is first bent back and forth, whereby the partition 51 of brittle material is broken and the liquids 49, 50 are mixed with each other so as to generate the required heat. The "cigarette" may of course also be inserted before the wall 51 is broken. In this embodiment, the mouthpiece 32 has micro-size through openings 52 to allow air to enter into the opening 36 through which the nicotine passes to cool the same before entering the mouth.

The above-described devices are made of a suitable heat-insulating material so that the mouthpiece 32 held between the lips will not become too hot and uncomfortable.

FIG. 5 illustrates an embodiment of the device according to the invention which takes the form of a pipe-bowl 10. The pipe-bowl, which may be made of wood or any other suitable material, defines in a conventional way a cup-shaped cavity 11 having a gas outlet 12 adjacent its bottom and an air inlet 13. The air inlet 13 may also be arranged in a cover 15 to be placed on the top face of the pipe-bowl 10. Along its sides and bottom, the cavity 11 has a heating element 14, e.g., in the form of a heating coil. This heating coil is connected to a battery 16 by an electronic circuit 17 including a manually operable switch and sensor (not shown) operating in the same way as the sensor 41. The battery is maintained in place by means of a screw plug 18. A pipe-stem 19 is connected to the bowl 10 by a threaded portion 20. The device according to FIG. 5 functions in substantially the same manner as the device according to FIG. 2, except for the fact that loose tobacco, and not a "cigarette", is placed in the receiving space 11.

We claim:
1. Tobacco compositions having a pH exceeding 7, for liberating essentially pure nicotine in effective amounts when air is drawn therethrough and when subjected to elevated temperatures below the combustion temperature of the tobacco, for inhalation purposes, comprising a mixture of tobacco, water, and added basic material.

2. Composition according to claim 1 characterized in that the water is present in the form of water-containing salt.

3. Composition according to claim 2 characterized in that the water-containing salt is selected from the group consisting of hydrated soda and zeolites.

4. Composition according to claim 2 characterized in that the basic material is selected from the group consisting of carbonates and hydroxides of sodium, potassium, and calcium.

5. Composition according to claim 2 characterized in that the water is present in 0.25-7 g $H_2O$/g tobacco.

6. Composition according to claim 1 characterized in that the water-containing salt is selected from the group consisting of hydrated soda and zeolites.

7. Composition according to claim 6 characterized in that the basic material is selected from the group consisting of carbonates and hydroxides of sodium, potassium, and calcium.

8. Composition according to claim 6 characterized in that the water is present in 1-5 g, $H_2O$/g tobacco.

9. Composition of claim 6, wherein the pH of the composition exceeds 8.8.

10. Composition according to claim 1 characterized in that the water is present in 1-5 g $H_2O$/g tobacco.

11. Composition of claim 10, wherein the pH of the composition exceeds 8.8.

12. Tobacco compositions for liberating essentially pure nicotine in effective amounts when air is drawn therethrough and when subjected to elevated temperatures below the combustion temperature of the tobacco, for inhalation purposes, comprising a mixture of tobacco, water, and added basic material, characterized in that the water and the basic material is present in the form of $Na_2CO_3.10\ H_2O$.

13. Composition according to claim 12 characterized in that the water is present in 0.25-7 $H_2O$/g tobacco.

14. Tobacco compositions for liberating essentially pure nicotine in effective amounts when air is drawn therethrough and when subjected to elevated temperatures below the combustion temperature of the tobacco, for inhalation purposes, comprising a mixture of tobacco, water, and added basic material, characterized in that the basic material is selected from the group consisting of carbonates and hydroxides of sodium, potassium, and calcium.

15. Composition according to claim 14 characterized in that the water is present in 0.25-7 g, preferably 1-5 g $H_2O$/g tobacco.

16. Tobacco compositions for liberating essentially pure nicotine in effective amounts when air is drawn therethrough and when subjected to elevated temperatures below the combustion temperature of the tobacco, for inhalation purposes, comprising a mixture of tobacco, water, and added basic material, characterized in that the water is present in 0.25-7 g $H_2O$/g tobacco.

* * * * *